United States Patent [19]
Laufer et al.

[11] Patent Number: 5,730,136
[45] Date of Patent: Mar. 24, 1998

[54] VENOUS PUMP EFFICIENCY TEST SYSTEM AND METHOD

[75] Inventors: Michael D. Laufer, Menlo Park; Gary H. Miller, Milpitas, both of Calif.

[73] Assignee: VNUS Medical Technologies, Inc., Sunnyvale, Calif.

[21] Appl. No.: 722,440

[22] Filed: Oct. 16, 1996

Related U.S. Application Data

[63] Continuation of Ser. No. 405,258, Mar. 14, 1995, abandoned.

[51] Int. Cl.$^6$ .................................................... A61B 8/00
[52] U.S. Cl. ........................................ 128/661.08; 128/691
[58] Field of Search .................. 128/660.08, 660.09, 128/660.1, 661.08, 661.09, 661.1, 662.06, 691, 694; 601/149, 150, 151, 152

[56] References Cited

U.S. PATENT DOCUMENTS

| | | |
|---|---|---|
| Re. 32,939 | 6/1989 | Gardner et al. ............................ 128/64 |
| 3,279,459 | 10/1966 | Schenker . |
| 3,461,855 | 8/1969 | Brown et al. . |
| 4,331,133 | 5/1982 | Arkans ................................... 128/87 |
| 4,574,812 | 3/1986 | Arkans . |
| 4,696,289 | 9/1987 | Gardner et al. ............................ 128/64 |
| 4,721,101 | 1/1988 | Gardner et al. ............................ 128/64 |
| 4,819,652 | 4/1989 | Micco ................................... 128/661.09 |
| 5,109,832 | 5/1992 | Proctor et al. ............................ 601/149 |
| 5,117,812 | 6/1992 | McWhorter ............................... 601/149 |
| 5,119,821 | 6/1992 | Tuchler ................................ 128/664.04 |
| 5,174,296 | 12/1992 | Watanabe et al. ...................... 128/660.09 |
| 5,179,941 | 1/1993 | Siemssen et al. ........................ 601/152 |
| 5,186,163 | 2/1993 | Dye ....................................... 601/152 |
| 5,207,226 | 5/1993 | Bailin et al. .......................... 128/661.08 |
| 5,218,954 | 6/1993 | van Bemmelen ........................... 128/24 |
| 5,327,774 | 7/1994 | Nguyen et al. ........................... 73/37 |
| 5,339,816 | 8/1994 | Akamatsu et al. ...................... 128/661.09 |
| 5,354,260 | 10/1994 | Cook ..................................... 602/13 |
| 5,406,948 | 4/1995 | Skidmore ............................... 128/661.1 |
| 5,575,762 | 11/1996 | Peeler et al. . |

FOREIGN PATENT DOCUMENTS

| | | |
|---|---|---|
| 0 127 157 A2 | 12/1984 | European Pat. Off. . |
| 0 329 489 A2 | 8/1989 | European Pat. Off. . |
| 0 343 969 A | 11/1989 | European Pat. Off. . |
| 0 582 462 A | 2/1994 | European Pat. Off. . |
| 2159076 | 6/1973 | France . |
| 2 211 616 | 7/1989 | United Kingdom . |

OTHER PUBLICATIONS

IEEE Transactions on Biomedical Engineering, vol. 35, No. 4, Apr. 1988, New York US, pp. 221–228, C.R. Bussani, et al.: "Improved Tracking of Limb Occlusion Pressure for Surgical Tourniquets".

Hobson II, Robert W. et al., "Current Status of Duplex Ultrasonography in the Diagnosis of Acute Deep Venous Thrombosis," in *Venous Disorders*, John J. Bergan, M.D. and James S.T. Yao, M.D., Ph.D., 1991, W.B. Saunders Company, pp. 55–62.

Nicolaides, Andrew N. et al., "Methods of Quantitation of Chronic Venous Insufficiency," in *Venous Disorders*, John J. Bergan, M.D. and James S.T. Yao, M.D., Ph.D., 1991, W.B. Saunders Company,, pp. 77–90.

Thomas, M. Lea, "Routine and Special Phlebography in the Evaluation of Venous Problems," in *Venous Disorders*, John J. Bergan, M.D. and James S.T. Yao, M.D., Ph.D., 1991, W.B. Saunders Company, pp. 123–136.

Strandness, Jr., D.E. et al., "Quantitation of Venous Reflux Using Duplex Scanning," in *Venous Disorders*, John J. Bergan, M.D. and James S.T. Yao, M.D., Ph.D., 1991, W.B. Saunders Company, pp. 137–143.

O'Donnell, Jr., "Popliteal Vein Valve Transplantation," in *Venous Disorders*, John J. Bergan, M.D. and James S.T. Yao, M.D., Ph.D., 1991, W. B. Saunders Company, pp. 284–295.

Brochure, Elcat Medical Systems, "Digital Photo–Plethysmography," *Dermatol Surg*, 1995, vol. 21.

Thibault, Paul K., "Duplex Examination," *Dermatol. Surg*, 1995, vol. 21, pp. 77–82.

Kistner, Robert L. et al., "1994 Update on Phlebography and Varicography," *Dermatol Surg*, 1995, vol. 21, pp. 71–76.

Bundens, Warner P., "Use of the Air Plethysmograph in the Evaluation and Treatment of Patients with Venous Stasis Disease," *Dermatol Surg*, 1995, vol. 21, pp. 67–69.

Fronek, Arnost, "Photoplethysmography in the Diagnosis of Venous Disease," *Dermatol. Surg*, 1995, vol. 21, pp. 64–66.

Weiss, Robert A. et al., "Continuous Wave Venous Doppler Examination for Pretreatment Diagnosis of Varicose and Telangiectatic Veins," *Dermatol Surg*, 1995, vol. 21, pp. 58–62.

Butie, Anton, "Clinical Examination of Varicose Veins," *Dermatol Surg*, 1995, vol. 21, pp. 52–56.

Tretbar, Lawrence L., "Deep Veins," *Dermatol Surg*, 1995, vol. 21, pp. 47–51.

Somjen, George M., "Anatomy of the Superficial Venous System," *Dermatol Surg*, 1995, vol. 21, pp. 35–45.

*Primary Examiner*—George Manuel
*Attorney, Agent, or Firm*—Fulwider Patton Lee & Utecht, LLP

[57] ABSTRACT

A test system and method for evaluating the efficiency of the venous pump in leg muscles and for identifying incompetent venous valves. The test system comprises a legging having inflatable bladders, a manifold and a system controller. A pressurized inflation source is provided which is in fluid communication with the manifold and the legging. The controller sequences valves within the manifold to inflate and deflate the bladders of the legging. The test system further includes a Doppler blood flow sensor interfaced to the controller. The sensor is configured with a housing which contains a rotatable disk, upon which two pairs of crystals are disposed. The sensor housing is secured a leg of a patient proximate a blood vessel in which blood flow is to be measured. The patient is positioned on a reclinable test station, upon which the controller and manifold may be mounted. The maximum volume of venous blood output from the leg is measured and the venous output flow is subsequently measured after the bladders are sequentially inflated above a first location on the leg of the patient. Reduced venous output flow from the maximum volume output indicates reflux and identifies the location of an incompetent valve.

40 Claims, 4 Drawing Sheets

VENOUS PUMP EFFICIENCY TEST SYSTEM AND METHOD

This application is a continuation of application Ser. No. 08/405,258 filed Mar. 14, 1995, now abandoned.

BACKGROUND OF THE INVENTION

This invention relates to a system and method for testing the efficiency of venous valves, and more particularly to a noninvasive device for testing the function of the venous pump in the leg muscles to identify incompetent venous valves.

The human venous system of the lower limb consists essentially of the superficial venous system and the deep venous system with perforating veins connecting the two systems. The superficial system includes the great saphenous vein and the small saphenous vein. The deep venous system includes the anterior and posterior tibial veins which unite to form the popliteal vein which in turn becomes the femoral vein when joined by the small saphenous vein. The venous systems contain a plurality of valves for directing blood flow to the heart.

Venous valves are usually bicuspid valves, with each cusp forming a sack or reservoir for blood which, under pressure, forces the free edges of the cusps together to prevent retrograde flow of the blood and allow only antegrade flow to the deep veins and heart. When an incompetent valve attempts to close in response to a pressure gradient across the valve, the cusps do not seal properly and retrograde flow of blood occurs. Venous insufficiency is a chronic disease in which incompetence of venous valves is thought to be an important factor in the pathophysiology.

Chronic venous insufficiency is a problem caused by hydrodynamic forces acting on the lowest part of the body, the legs, ankles and feet. As the veins dilate due to increased pressure, the valves in the veins become less able to withstand the weight of the blood above them. The weight of the blood causes the veins to dilate further and the valves in the veins to fail. Localized incompetence of a venous valve allows reflux of blood from the deep venous system to the superficial venous system. Such incompetence is traditionally thought to arise at the saphenofemoral junction, but may also start at the perforating veins.

Patients who develop or have chronic venous insufficiency of the lower extremities frequently develop complications of this disease. These manifestations range from skin discoloration to painful varicose veins, to disabling skin ulcerations. Frequently, these patients also develop blood clots in their legs which can travel to their lungs, resulting in death from pulmonary embolism.

Patients who develop these complications do so over time, with increasingly severe damage to the veins and valves within the veins. Certain surgical procedures can help correct or mitigate the progression of the disease. However, correct diagnosis requires evaluation of the veins and valves at segmental levels of the leg, with therapy directed specifically to the type and level of disease present. Vein incompetence at the ankle or calf requires treatment different from venous incompetence which has affected the veins in the upper leg. Diagnosis requires specific morphological information. The international scheme for categorization of venous disease requires this morphological information. Further, researchers must compare patients by classifying them morphologically in order to be able to compare results of treatments.

The current "gold standard" for morphology of venous disease is the descending renogram. This study requires that patients have an intravenous catheter placed in their groin and have multiple injections of radiographic contrast material injected while having multiple x-rays taken of the legs. The patient is held in various positions and tilted to allow the contrast material to flow into the veins.

The descending renogram test has many limitations. For example, the contrast agent has inherent medical risks of allergic or anaphylactic reactions. Also, the test requires that needles and canulas be placed into the patient at multiple sites for dye injection. In addition, it is a static test and does not provide information about dynamic blood flow in the veins. Furthermore, the descending renogram may give data which is artifactual, because the dye may cause renoconstriction or dilation and change the valvular function.

Another test to determine venous incompetency is the duplex ultrasound. This test gives good information regarding locating the point(s) of incompetence and determining vein size. If color-flow is added, then duplex ultrasound can differentiate veins from arteries. In addition, the test can be used to localize perforating vessels. The primary limitation of duplex ultrasound is that it is extremely operator dependent, making it difficult to reproduce results from one institution to the next. Additionally, duplex ultrasound is a test which can only provide information about the existence and patency of vessels, and is much less useful in providing a functional assessment of the venous system.

The directional handheld Doppler can provide information about flow direction in a given vessel. With proper usage, information about valvular competence and venous flow through the superficial and parts of the deep system can be obtained. However, results from the directional handheld Doppler is highly dependent upon the technician performing the test. The angle of the Doppler probe in two axes, the thoroughness of the test and the consistency of the provocative tests (usually valsalva and manual leg compression) all are possible sources of variability. Also, the handheld Doppler does not provide information regarding quantification of flow, size of the vessels, or direction of flow. Similarly, the handheld Doppler does not indicate competence of perforating veins, especially in the calf where the distance between the skin surface and the vessel is greater than the rest of the leg. Moreover, the usefulness of the handheld Doppler is limited by the presence of large varicose veins and cannot be used effectively on patients who have had recanalization with unpredictable anatomy.

Air impedance plethysmography is a test wherein an air bladder is placed about the lower leg and inflated only to sufficient pressure to make contact with the skin throughout the surface of the bladder. Plethysmography works by measuring the change in volume of the lower leg with exercise and as the leg is moved from a horizontal to a vertical dependent position. The rate of filling for normal venous systems has been empirically determined. More rapid filling in moving to a dependent position is a sign of possible venous valve incompetence. Additionally, the change in volume with tip-toe exercise can be measured and provides data about the output of blood resulting from the calf muscle pump. This can be combined with a tourniquet placed around the leg just tightly enough to obstruct flow through the superficial veins. Some practitioners believe that the deep vein function can be isolated in this manner; however, such a belief is not completely accepted by the medical community.

While air plethysmography is less dependent on the operator's skill than the other tests previously described, it is limited to measuring venous function in the lower leg. Air plethysmography is also incapable of further delineating or localizing the point(s) of incompetence, since perforating vein incompetence results in the same changes in venous filling rates as deep or superficial vein incompetence. Hence, while being a fairly reproducible test of lower leg calf pumping function, air plethysmography does not provide anatomical or morphological information which is needed for patient disease classification and treatment.

Photoplethysmography is identical to the tip-toe air plethysmography described previously, except that the transducer is a LED/photodetector pair which is mounted on the skin, instead of an air bladder. The amount of blood in the skin changes with exercise and results in a tracing similar to that resulting from the air plethysmograph. The disadvantages of photoplethysmography are the same as those described herein for air plethysmography.

Testing methods employing devices having mercury in silastic and pneumoplethysmography were predecessors to impedance plethysmography and photoplethysmography tests discussed above. The impedance plethysmography test included a tourniquet placed on the thigh and another on the calf which was attached via a pressure transducer to an amplified strip chart recorder. The leg would be elevated so as to drain the blood. The cuff on the thigh would be inflated to just above venous pressure. The leg then would be lowered and the patient would stand. The tourniquet would be quickly released and the venous filling time would be measured, as described for air and photoplethysmography. The criteria for normalcy was determined empirically by testing normal legs. A more rapid filling time would indicate venous reflux.

Although relatively reproducible, impedance plethysmography has the same limitations as air and photoplethysmography, but required more coaching from the technician and was, therefore, more technician dependent. Blood clots in the vein can produce false negatives in plethysmography tests by reducing the change in volume, since the fixed volume of the clot prevents additional blood from entering the vessel. Plethysmography tests also require that the patient is able to stand.

There is a great need for a diagnostic system which would provide functional assessment about the ability of the veins to conduct blood back to the heart. Such a system would provide a morphologic assessment about the level at which the veins are failing. Similarly, there is need for a diagnostic system that differentiates deep from superficial and perforating vein function. Moreover, a diagnostic system is needed that provides quantitative assessment for comparison over time and after an intervention. Preferably the ideal system also would be only minimally dependent on technician skill, so as to be reproducible and comparable from day-to-day and institution-to-institution. The system and method of the present invention provides these features while solving many of the deficiencies found in the prior art test systems.

SUMMARY OF THE INVENTION

Briefly, and in general terms, the present invention provides a system and method for testing the efficiency of the venous pump in leg muscles and for identifying incompetent venous valves. The system includes a test station at which a patient is connected to a pneumatic legging having a plurality of air inflatable bladders. The bladders are connected to a manifold, which is connected to a system controller. The controller restricts the blood flow in the patient's leg by sequentially inflating the bladders in the legging. The controller receives femoral blood flow measurements from a Doppler flow transducer.

The test performed by the system and method of the present invention is non-invasive, while providing both morphological and functional data. The test results are not operator dependent, and, therefore, are highly reproducible. Similarly, the testing can be performed without patient effort being a determining factor. Moreover, the results are auto-standardized so that there is no dependency on empirical population-based data. Consequently, pre-intervention and post-intervention studies can be compared in the same patient and results can be compared from different medical centers. Thus, results from new therapies can be correlated and evaluated against other existing modalities. In addition, the system design allows it to potentially predict results after a successful venous valve repair procedure. Also, the format of the output from the controller is easily configured to be understood by the referring physician and vascular surgeon.

The present test system comprises a legging or stocking having inflatable bladders, a manifold and a system controller. The manifold includes valves in fluid communication with inflation tubes connected to the inflatable bladders of the legging. A pressurized air source is provided which is in fluid communication with the manifold and the inflation tubes. The controller sequences the valves in the manifold to inflate and deflate the bladders of the legging. The test system further includes a blood flow sensor interfaced to the controller, e.g., a Doppler flow transducer. The controller uses a microprocessor for coordinating the flow sensor measurements with the bladder inflation sequence. The patient is positioned on a reclinable test station, upon which the controller and manifold may be mounted.

The test system's Doppler blood flow transducer is configured with a first pair of crystals and a second pair of crystals directed at 180 degrees in opposite direction to the first pair of crystals. The sensor is configured with a housing which contains a rotatable disk, upon which the two pairs of crystals are disposed. A strap or similar mechanism is used to secure the housing proximate to a location on a leg of a patient corresponding to a vein or artery for which blood flow is to be measured. The controller causes a pulsed sound signal to be emitted and received through the crystal pairs for measuring blood flow in the patient's vein or artery, such that the sound signals are centered within the blood vessel. The sensor can also measure the distance between the walls of the blood vessel.

The method in accordance with the present invention determines the location of an incompetent venous valve in a leg of a patient. The method uses a legging having bladders or a similar device to sequentially restrict the blood flow along the veins in a patient's leg. The total or maximum output flow from the leg is measured and the blood flow is subsequently measured after the bladders are sequentially inflated above a first location on the leg of the patient. Reduced output flow from the maximum flow indicates reflux and identifies the location of an incompetent valve. Further steps of the method include restricting the blood flow at a higher locations on the leg of the patient and measuring the output blood flow through the femoral vein of the patient.

These and other features and advantages of the present invention will become apparent from the following more detailed description, when taken in conjunction with the accompanying drawings which illustrate, by way of example, the principles of the invention.

DESCRIPTION OF THE PREFERRED EMBODIMENTS

Figure 1:
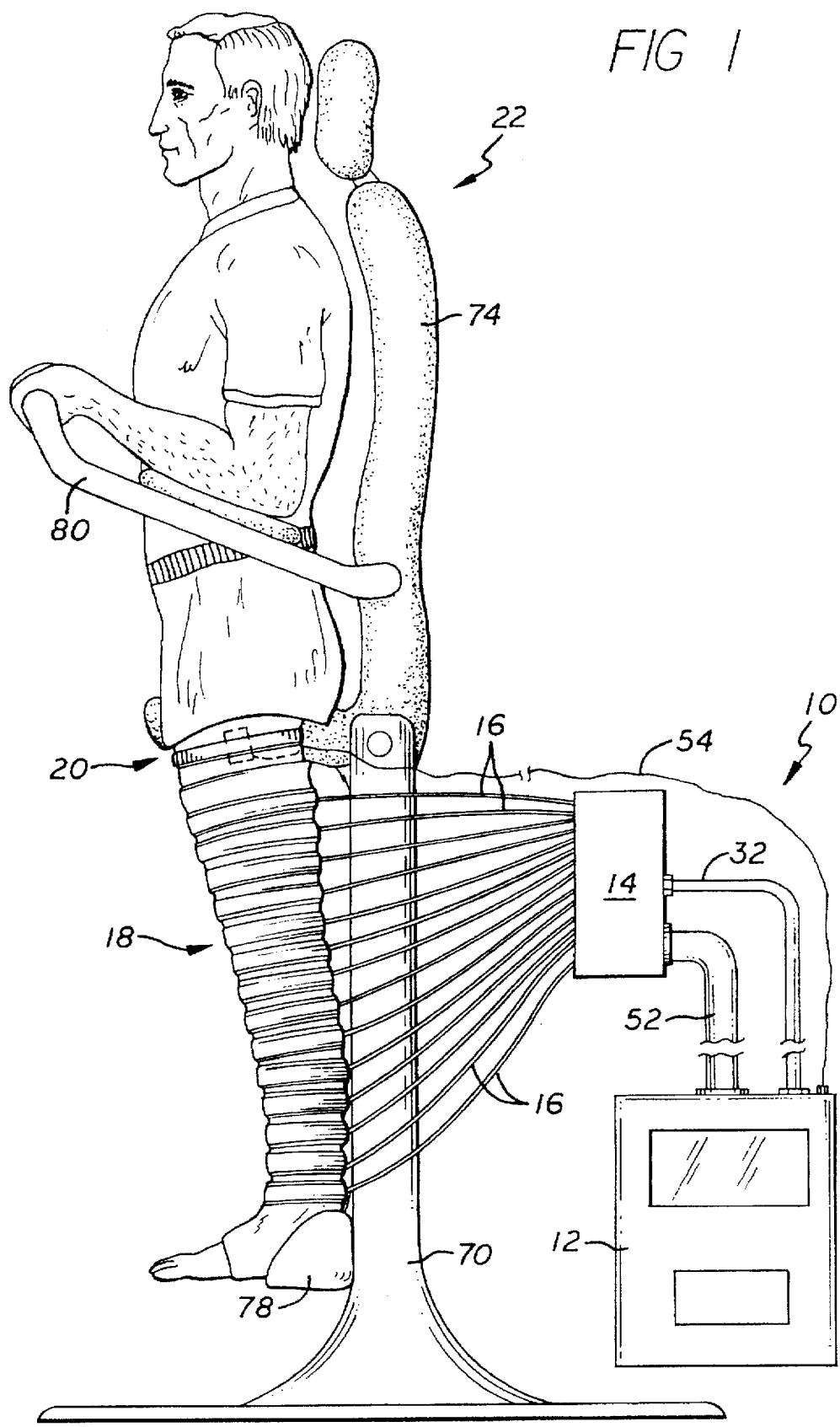
FIG. 1 is a side plan view of the test system of the present invention showing a patient prepared for testing disposed within a pneumatic legging attached to a manifold and system controller.

As shown in the exemplary drawings, the invention is embodied in a diagnostic system 10 having a controller 12 connected to a manifold 14 by a plurality of inflation tubes 16 which are further connected to an inflatable legging 18. A Doppler flow transducer 20 strapped to the upper thigh of a patient provides measurements of blood flow in the femoral vein to the controller. As shown in FIG. 1, the patient is positioned on a test station 22 so that he or she may be moved to positions where the foot is elevated equal to the level of the heart.

It is possible to mimic valvular competence with dynamic tourniquet obstruction. Externally compressing a vein and preventing it from filling simulates closing a venous valve at the point of the tourniquet. Furthermore, the muscle pump function can be mimicked by external compression of the leg by a pneumatically inflated series of tourniquets. The narrower each tourniquet, the higher is the resolution of the device.

In accordance with the present invention, multiple pneumatically activated tourniquets may be placed along the lower and upper leg to empty the blood in the veins of the leg. Emptying of veins in this way is similar to the use of an Esmark bandage, whereby an arterial tourniquet is placed on the high thigh and an elastic bandage is wrapped around the leg from foot to thigh, upon which the arterial tourniquet is inflated to keep the leg vessels empty of blood. The deep veins can be isolated from the superficial veins by controlling the pressure of inflation in the bladders at each level.

By measuring venous outflow through the only normal exit vessel, the common femoral vein, and by taking measurements with the leg level with the heart and dependent (but without muscular activation) one can account for changes in arterial inflow due to position change. In addition, the amount of blood outflow can be obtained, as a proportion of maximum flow. By measuring the changes in outflow with compression and "competent valve simulation," one can determine morphologically where the valvular incompetence exists. Because of the resolution between tourniquets, it is possible to demonstrate perforator incompetence separate from longitudinal vein incompetence. Finally, with the tip-toe exercise, a measurement of calf pump output efficiency can be obtained.

Figure 2:
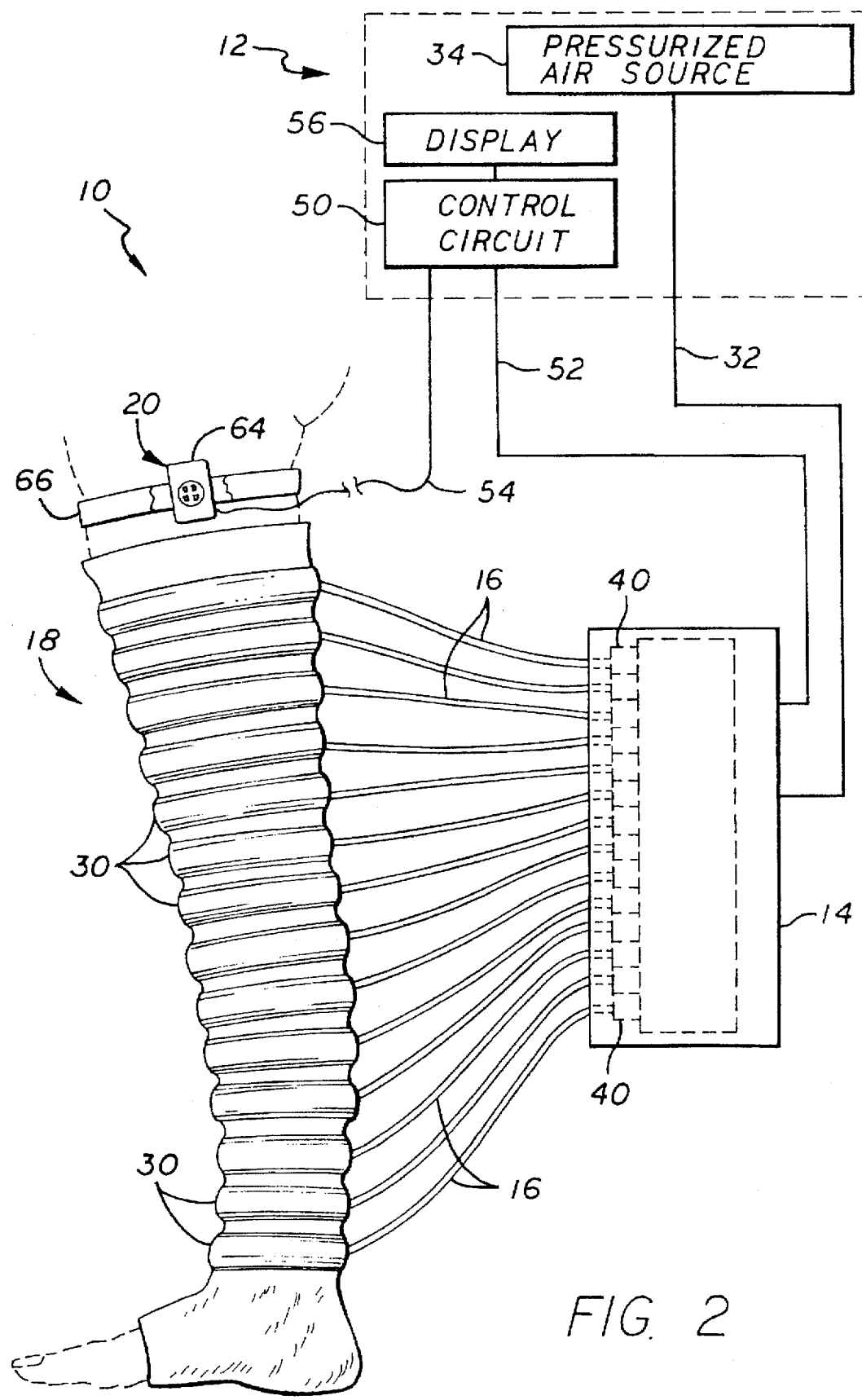
FIG. 2 is a side plan view of the test system of the present invention and partial schematic showing the system controller, manifold, inflation tubes, legging and doppler flow transducer and their interconnections.

As shown in FIG. 2, the test system 10 includes a long-leg tubular legging 18 having a series of inflatable bands or bladders 30. The legging has a longitudinal slit 105 in the back so that the legging may be wrapped around the patient's leg. Each bladder or cuff is substantially cylindrical in shape, having first and second ends which abut at the back of the legging. The semicircular or "C-shaped" bladders are spaced approximately equally apart along the legging, wrapping around the patient leg.

Forming cuffs 30 with closed ends in the back of the legging 18, the bladders have a relatively small diameter at the ankle, progressing to the largest diameter cuff at the upper thigh. The legging is preferably made of a material such as coated cotton or vinyl; whereas, the bladders are made of a fluid tight material capable of maintaining the liquid or gas used for inflation, such as rubber or vinyl. The legging may be disposable, such that the body is constructed from molded or a sheet of heat sealed plastic. Similarly, the bladders may be formed as an integral part of the legging body.

Each bladder 30 may be connected to an inflation tube 16 which is attached to a coupling or manifold 14 in fluid communication with a pressurized fluid source 34. Alternatively, the bladders may be connected directly to the coupling. The inflation tubes are made from material suitable to contain the fluid at inflation pressures, such as rubber or nylon. The pressurized fluid is provided to the manifold through a similarly constructed conduit 32.

Pressurized air, oxygen, carbon dioxide, or other suitable gas is provided to the manifold 14 from a source 34 located in the controller 12. Alternatively, the gas source may be external to the controller. Similarly, a hydraulic system, rather than a pneumatic system, may be utilized to inflate the bladders, for example, with water or oil. The materials of construction disclosed herein are by way of example only, and are not intended to limit the scope of the invention.

Figure 5:
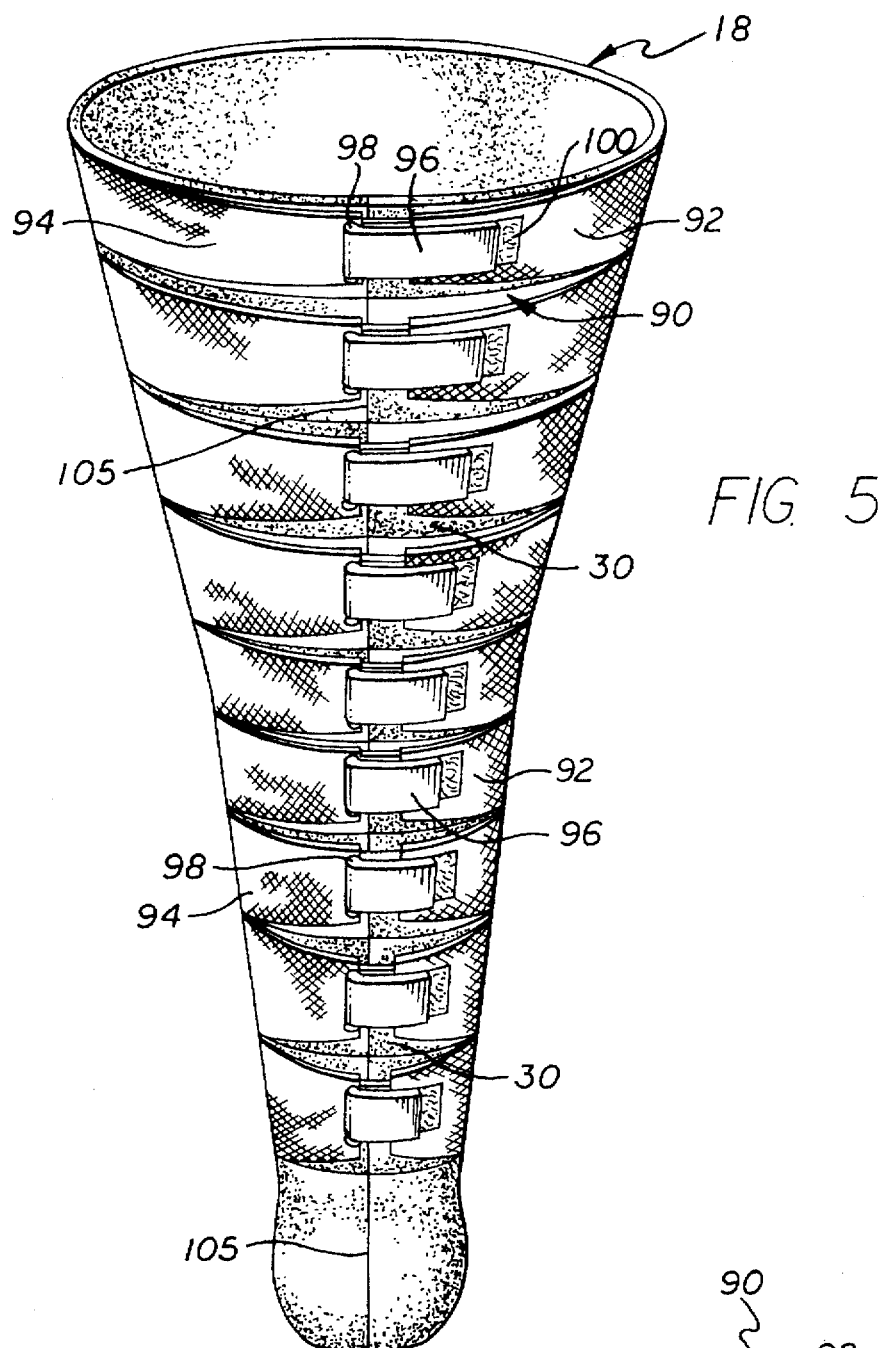
FIG. 5 is a rear perspective view of the legging of FIG. 2, showing a closure system.
Figure 5A:
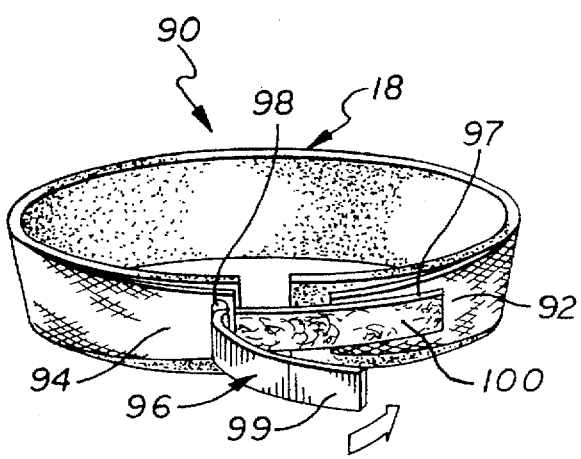
FIG. 5A is a partial rear perspective view of the enclosure system of FIG. 5 showing a strap and fastener.

As shown in FIGS. 5 and 5a, a closure system 90 may be used with the legging 18 to configure the test device for different size patient legs. A plurality of first tapered tabs 92 are secured to or manufactured as part of the legging and extend from one outside edge to the center of the back of the legging. A plurality of second tapered tabs 94 are similarly secured to or manufactured as part of the opposite side of the legging and extend to the center of the back of the legging proximate to the end of the corresponding first tapered tab. The plurality of sets of first and second tabs are spaced approximately equally apart from the ankle to the upper thigh.

In the closure system 90, a strap 96 is fixed at its first end 97 to one side of each first tapered tab 92 and is configured to be slidably disposed within a slot 98 in the corresponding second tapered tab 94. The strap's second end 99 is removably secured to the first tapered tab by a suitable fastener affixed to either the first end of the strap or directly to the first tapered tab, for example, by a hook and loop connector (VELCRO®), snap or buckle. The strap is used to tighten the first and second tapered tabs together to adapt the legging to the diameter of the patient's leg. The legging is secured sufficiently tight around the leg to effect a tourniquet when the cuffs 30 are inflated; however, the closed legging should not be unduly tight around the leg when the cuffs are deflated.

Referring to FIG. 2, the coupling manifold 14 houses multiple electrically or pneumatically activated valves 40. The manifold is preferably constructed from a plastic, such as polycarbonate, and may be mounted on the test station 22. The manifold valves can be selectively opened to pass air to each connected bladder 16, opened to vent air from the bladder or left closed to maintain bladder pressure. Pressure monitoring is accomplished through a pressure transducer (not shown) in the air conduit 32 or at the source 34.

Sequencing of the valves is initiated by a control circuit 50 disposed within the controller 12. The control circuit is connected to the valves by standard electronic cabling or pneumatic tubing shielded within conduit 52.

As shown in FIG. 2, the controller 12 includes a microprocessor or similar control circuit 50 which operates the manifold valves 40. The sequence of inflation and deflation of the bladders 30 is controlled by sequentially opening and closing the manifold valves. The sequencing may be accomplished by software in the microprocessor or by an equivalent electronic or mechanical device. In addition, the control circuit communicates with the Doppler flow sensor 20 via a sensor lead 54 to coordinate the valve sequencing with the blood flow measurements. The pressure of the inflation fluid is monitored by a sensor (not shown) in the conduit 32. The pressure signals are transduced, amplified and recorded by the controller.

The data gathered by the controller 12 and the location of any incompetent valves or similarly computed information are sent to a printer via a standard communication port (not shown). The interpretation of the study is also programmed with user configurable text phrases and output patterns, for example, using a forty character LCD display. Output displays may be available to provide pressure and blood flow data and to provide system error messages. Similarly, touch keys may be configured to interface with the controller to initiate and/or terminate the testing and to allow input of test parameters and patient specific data.

Figure 3:
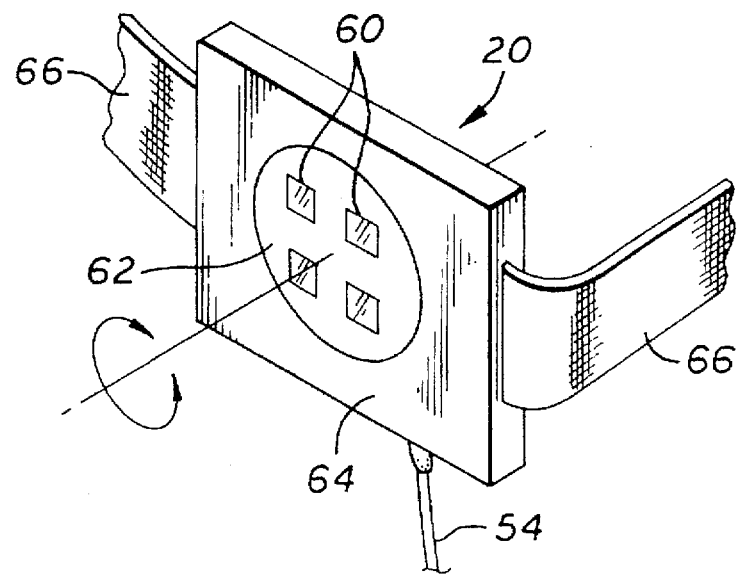
FIG. 3 is a front perspective view of the Doppler flow transducer, housing and sensor lead.

As shown in FIG. 3, the Doppler transducer 20 comprises two pairs of crystals 60 mounted on a surface 62, such as a rotatable disk, disposed within a housing 64. Each crystal pair is directed 180 degrees from the other pair and secured at about a thirty to forty-five degree angle of incidence to the contact surface of the leg (sixty to forty-five degrees from the mounting surface). The transducer is connected to a pulse Doppler generator (not shown) located within the controller 12. The pulse Doppler generator causes the crystal to emit and detect sound signals which may be interpreted for a Doppler frequency shift by the control circuit 50. The disk is rotated by a microprocessor-controlled motor, rotor or other device (not shown) also located within the transducer housing. The housing is secured to the patient thigh by a strap or similar mechanism.

When the Doppler transducer 20 is in operation, the disk 62 is rotated while the legging bladders 30 positioned at the patient's leg are sequentially inflated. Thus, the sound signal frequency shift produced by the distally directed crystals is equal to the signal magnitude produced by the proximally directed crystals. The signals from the crystal pairs, however, will be opposite in direction, such that one signal is increasing and the other signal is decreasing. This rotation verification assures that the crystals are pointed along the long axis of the vein. An inability to accomplish this results in control circuit 50 generating an error message at the display 56 and the technician is prompted to reposition the device.

The pulse timing sequence is then changed by the control circuit 50 so that the center of the vessel is located, and so that the size of the vessel is calculated by the controller 12. Determining these parameters allows the control circuit to make uniform measurements of the fluid velocity and to make uniform calculations of the fluid flow. The control circuit calculates the fluid flow at the center of the vessel. Assuming a round vessel, the volume of blood flow in a given period of time is calculated as the integral over time of the velocity of the blood times the cross-sectional area of the blood vessel.

As noted, the Doppler flow transducer 20 is configured with two paired transmitter/receiver units 60. One crystal of each pair is configured to transmit a pulsed sound signal, while the other crystal of each pair is configured to receive the reflection of the pulsed signal. The transmitting crystals are driven by a frequency generator within the controller 12 which causes the transmitter crystals to intermittently send a sound signal. The frequency of any sound signal reflected back is detected by the receiving crystal in the pair.

The frequency shift (Doppler) is interpreted by the control circuit 50. If the sound signal is reflected from moving blood cells, then the frequency of the signal is changed upward by blood moving toward the receiving crystal and downward by blood moving away from the crystal. By configuring two pairs of crystals 180 degrees offset from each other, the magnitude of the flow represented by the Doppler shift will be equal from each pair, but will be opposite in direction, so long as the crystal pairs are sensing along the same long axis of the vessel. By turning the sensor's rotatable disk 62 until the Doppler shift is equal, but opposite, one can effectively set the crystals parallel to the blood flow in the vessel.

To obtain reproducible blood flow measurements, the sensor 20 must consistently measure from the same place within the blood vessel. The most accurate place to measure average flow is in the center of the vessel's cross section. By using a pulsed Doppler transmitter and sensor combination, one can not only place the field of measurement into the center of the vessel, but can also obtain relatively accurate measurements of the flow in that vessel. The flow measurement requires a calculation of the integral of flow over time multiplied by the cross-section of the vessel. Because flow is not constant but instead is pulsatile, a calculational integration is necessary for accurate measurement.

The method of accomplishing this "centering" requires determining the location of the back wall and front wall of the vessel. The vessel diameter is calculated from the wall locations and the control circuit 50 sets the timing of the send/receive crystal pair to the midpoint of the vessel diameter. For instance, the control circuit initiates the transmitting crystal to send or emit a short sound signal and uses the receive crystal to detect the reflected signal at some interval of time. By changing that interval, the flow measured changes. As the interval is lengthened, the flow measured changes until a point when it reaches zero. When the interval is long enough, the sound travels past the back wall and is no longer reflected. The distance to the back wall is calculated as a function of the first interval of time when the signal is not reflected and the speed of sound through the tissue in the leg.

The time interval between when the first crystal sends its signal and when the control circuit 50 detects the reflected signal in the second crystal is then shortened incrementally until no Doppler shift is calculated (i.e., zero flow). The first time interval where no shift is detected is used to calculate the distance to the front wall of the vessel. The difference in distance from the front to the back wall divided by two is the measured midpoint of the vessel. The control circuit then sets the send/receive interval to the computed time in which a signal will travel from the first crystal to the vessel's midpoint and back to the second crystal of the same pair. The control circuit "listens" to the vessel's center for the remainder of the test.

Because the system of the present invention creates flow by compressing the veins with pneumatic cuffs, the impulse and blood flow measured by the sensors during this "set up" or calibration phase can be relatively consistent. The timing of the cuff compression and transmitted sound can be empirically set to maximize the flow and therefore the accuracy of the centering and axial localization phases of the calibration.

Figure 4:
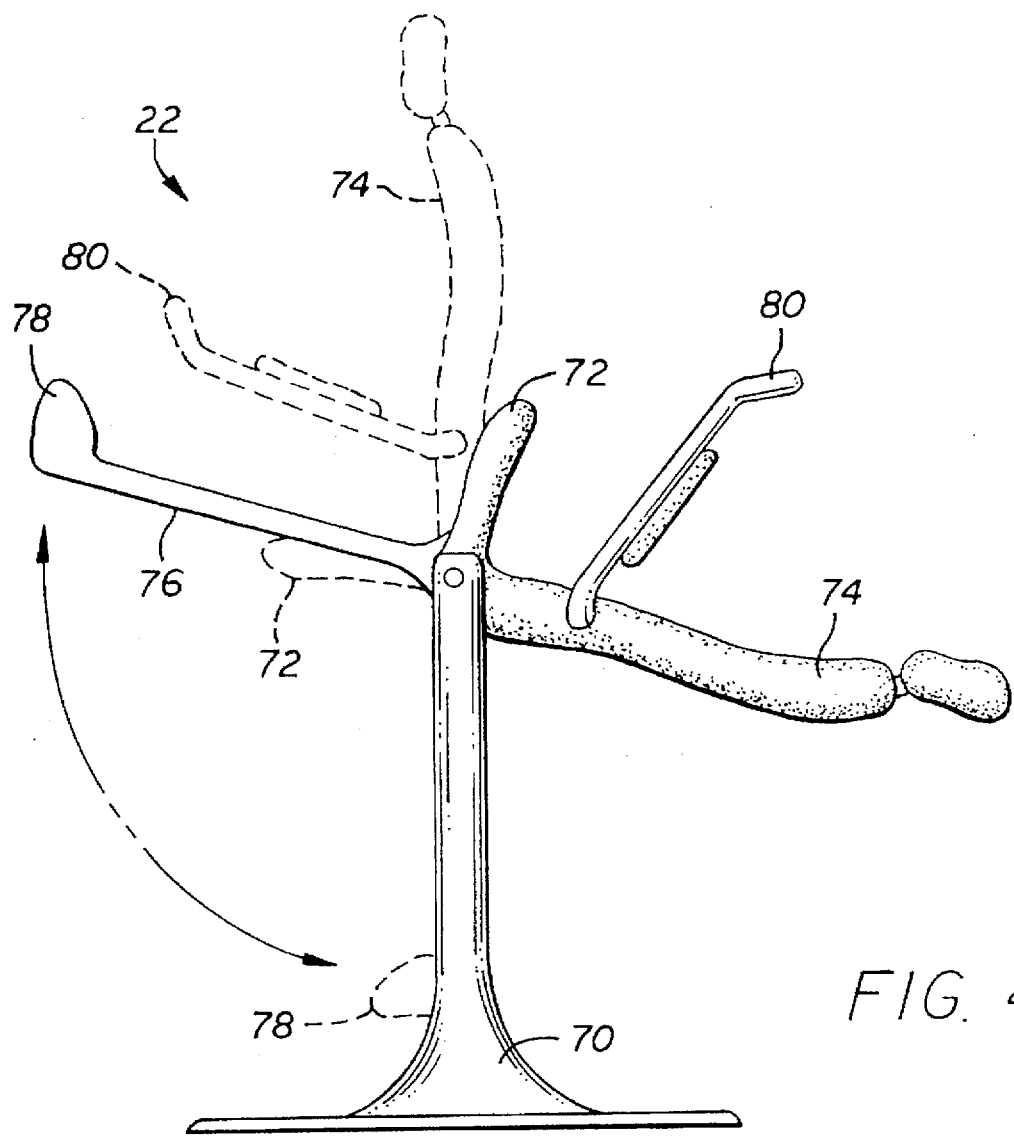
FIG. 4 is a side plan view showing the testing station, including the stand in a vertical position and the frame, seat and backrest rotated to a horizontal position.

As shown in FIG. 4, the testing station 22 is configured with a central stand 70, a bicycle-type seat 72 and backrest 74 secured to a reclinable frame 76 for positioning the patient. This assembly can be pivoted backward so that the seat backrest is horizontal. In addition, there is a cup-like device 78 affixed to the bottom of the station frame. The cup accommodates the patient's heel, and there is one heel cup on each side of the frame. A handrail 80 is secured to the backrest or frame so the patient may balance himself or herself when the frame is rotated to the horizontal position. The controller 12 electronic and mechanical components and the manifold 14 may be part of or mounted to the test station stand or frame.

The patient is seated on the seat 72 of the test station 22 with his or her back against the rest 74 and heels in the cups 78. The inflatable legging 18 is placed on the patient's leg and closed by a zipper or closure system 90 as described heretofore. The manifold 14 is connected to the controller 12 via main air conduit 32 and electrical conduit 52. The Doppler sensor 20 is attached to the patient over the common femoral vein proximal to the entry point of the greater saphenous vein. The patient is tilted back on the station frame 76 so that his or her legs are at the same level above the floor as the patient's heart.

Each patient leg is tested and studied separately. First, the control circuit 50 calibrates the Doppler transducer 20 to assure that the transducer is properly centered over the femoral vein. The bladders or cuffs 30 in the legging 18 are inflated from the ankle or foot to the upper thigh in sequence so as to cause restrictions which milk the blood out of the leg. The cuffs are inflated sufficiently to compress the veins, but not compress the arteries. The pressure in the cuffs caused by the sequence of restrictions is high enough to force blood out of the deep and superficial veins. The volume of venous output blood flow through the leg (femoral vein) is calculated by the control circuit and is termed the Maximal Venous Output (MVO).

The cuffs 30 are deflated by the controller 12 and the patient is tilted so that the legs are dependent. The patient is instructed not to move his or her legs. The control circuit 50 again centers the Doppler transducer 20. The cuffs are then inflated by the controller sequentially from foot to thigh and the venous output blood volume is again calculated by the control circuit. This volume of venous output blood flow through the leg (femoral vein) is termed the Maximal Dependent Output (MDO).

The patient is left in this position with legs dependent. The controller 12 then sequences inflation and deflation of the cuffs 30 to test venous valve competence and pump output efficiency at each level of the leg. To begin the procedure for identifying the location of an incompetent valve, the controller inflates the lowest or first cuff (closest to the ankle). This pushes blood to the level of the next cuff above the first cuff, i.e. the second cuff, which remains deflated. The controller then releases or deflates the first cuff. If the venous valve at the location of the first cuff is competent, then the blood pushed above the first valve will remain above the valve. If that valve, however, is incompetent, then some or all the blood pushed above the first valve will reflux below the valve.

The control circuit 50 inflates the second cuff and the remaining upper cuffs to the upper thigh are inflated in sequence to milk the blood out of the leg and past the diagnostic flow sensor 20 at the common femoral vein. The controller 12 uses the signal from the flow sensor placed proximate the upper thigh proximate the femoral vein to calculate the total volume of blood which flows out of the leg after the first valve was released. Any difference in flow between this measurement and the MDO is the amount of reflux at the first cuff level.

If the valves proximate the first cuff are competent, then the blood moved by the compression by the first cuff prior to its deflation will remain at that level for the other cuffs to push out. Thus, the measured volume of blood flow for a test at a competent valve will approximate the MDO. If the valves are incompetent, the blood will regurgitate back down and the amount of blood pumped out will be less than the MDO by the amount which refluxes through the incompetent valves.

The test is repeated, except that this time the first and second cuffs are inflated to move the blood in the leg past the second cuff. The first and second cuffs are deflated to permit blood to drain through any incompetent valves proximate the second cuff. The third cuff (next above the second cuff) and all subsequently higher cuffs are then inflated to move the blood past the flow sensor. The total blood flow is again calculated for this valve sequence. This venous output will indicate any reflux at the level of the second cuff when compared to the MDO. Such valve sequencing is repeated until the top most cuff is tested.

The evaluation of each leg is then repeated, except that instead of compressing to the point of deep venous compression, the cuffs are initially compressed fully, then deflated to superficial vein compression only. At this compression, differences in flow represents incompetence of the deep veins, whereas previous measurements were for total vein reflux. Location of deep venous valves as well as perforators which are incompetent can be determined in this way. Additionally, the incompetence of the saphenofemoral junction can be ascertained in this manner.

Another evaluation can be accomplished by having the patient perform a tip-toe exercise while measuring venous output as described heretofore. The measured blood flow volume divided by the MDO is the Dependent Pump Efficiency (DPE). A similar evaluation can be obtained with the patient supine, such that the measured venous output divided by the MVO represents the Maximum Pump Efficiency (MPE). The difference between the DPE and MPE is the amount of decrease in efficiency due to the longitudinal valvular incompetence, since the incompetence of the longitudinal vein is decreased to near zero by eliminating the effect of gravity.

By appropriately timing the cuff inflation at selected levels, and combining this with tip-toe exercise, the test system is capable of predicting the improvement which one might get by re-establishing valvular competence at any given level, or at multiple levels in combination. The timing sequence would be determined empirically by changing the time between calf muscle contraction and inflation until the maximum pump output was obtained Maximal Compensated Pump Output, MCPO.

Additionally, an evaluation may be performed which simulates the efficiency of the venous pump likely to be gained by valve repair. During the procedure, the patient is allowed to stand with the Doppler flow sensor in place over the femoral vein. The patient is asked to do a tip-toe exercise and the total volume of output blood flow is calculated. This is then compared with the MDO. Additionally, the effect of valve repair can be assessed by doing a similar exercise as above, but instead of allowing the blood to flow as it naturally would, the cuff at the level of proposed valve repair would be inflated at the appropriate time after tip-toe to maximize venous outflow. The increase of venous blood volume over baseline would be the approximate improvement which a venous repair could expect to achieve.

Thus, the test system method of the present invention meets the need for a diagnostic system which provides analysis of the ability of the veins to conduct blood to the heart. Also, the system provides a morphologic assessment as to the level at which the veins are failing. In addition, the system differentiates deep from superficial and perforating vein function. Moreover, the present system provides quantitative assessment for comparison over time and after an intervention, being only minimally dependent on technician skill, so as to be reproducible and comparable from day-to-day and institution-to-institution.

While several particular forms of the invention have been illustrated and described, it will be apparent that various modifications can be made without departing from the spirit and scope of the invention. Accordingly, it is not intended that the invention be limited, except as by the appended claims.

What is claimed is:

1. A non-invasive method for determining total venous blood output from a leg of a patient, the method comprising:

sequentially restricting venous blood flow along a leg of a patient from a first location proximate an ankle of the leg to a last location proximate an upper thigh of the leg, wherein venous blood in the leg is moved from the first location to the last location; and determining a total volume of outlet blood flow through a vein in the leg in response to said sequentially restricting step.

2. The method of claim 1, wherein said determining step includes measuring a diameter of a femoral vein proximate the last location and measuring a flow rate of blood through the femoral vein proximate the last location.

3. A non-invasive method for determining venous competence, the method comprising:

providing a sequence of restrictions along a leg of a patient from a first location to a second location such that venous blood in the leg is moved from the first location to the second location, wherein the first location is between an ankle of the leg and the second location;

releasing the sequence of restrictions to permit venous blood to flow from the second location to the first location;

subsequently sequentially restricting venous blood flow along the leg from the second location to a last location proximate an upper thigh of the leg, such that venous blood in the leg is moved from the second location to the last location;

measuring a first volume of outlet blood flow from the leg in response to said subsequently sequentially restricting step; and comparing the first volume of outlet blood flow to a total volume of outlet blood flow to determine venous competence below the second location on the leg.

4. A non-invasive method for determining venous competence, the method comprising:

sequentially restricting venous blood flow along a leg of a patient from a first location proximate an ankle of the leg to a last location proximate an upper thigh of the leg, wherein venous blood in the leg is moved from the first location to the last location;

determining a first volume of outlet blood flow through a vein in the leg in response to said sequentially restricting step;

providing a sequence of restrictions along the leg of the patient from a first location to a second location such that venous blood in the leg is moved from the first location to the second location, wherein the second location is between the first location and the last location;

releasing the sequence of restrictions to permit venous blood to flow from the second location towards the first location;

subsequently sequentially restricting venous blood flow along the leg from the second location to the last location, wherein venous blood in the leg is moved from the second location to the last location;

determining a second volume of outlet blood flow from the leg in response to said subsequently sequentially restricting step; and comparing the second volume of outlet blood flow to the first volume of outlet blood flow to determine venous competence below the second location on the leg.

5. The method of claim 4, further comprising the step of determining venous incompetence, wherein venous incompetence is identified at the second location when the second volume of outlet blood flow is substantially less than the first volume of outlet blood flow.

6. The method of claim 4, further comprising the step of providing a legging having inflatable bladders for sequentially restricting venous blood flow at a plurality of locations on the leg of the patient.

7. The method of claim 4, wherein said determining a first volume of outlet blood flow step includes measuring a diameter of a femoral vein proximate the last location and measuring a flow rate of blood through the femoral vein proximate the last location.

8. The method of claim 7, wherein said determining a first volume of outlet blood flow step further includes providing a Doppler flow transducer and a microprocessor interfaced with the transducer.

9. A non-invasive method for determining competence of deep veins in a leg of a patient, the method comprising:

providing a sequence of restrictions along a leg of a patient to compress superficial veins and deep veins from a first location to a second location such that venous blood in the leg is moved from the first location to the second location, wherein the first location is between an ankle of the leg and the second location;

releasing the sequence of restrictions sufficient to permit blood to flow through the deep veins from the second location to the first location, wherein said releasing step retains the sequence of restrictions sufficient to prohibit blood flow through the superficial veins;

subsequently sequentially restricting venous blood flow along the leg from the second location to a last location proximate an upper thigh of the leg, wherein venous blood in the leg is moved from the second location to the last location;

measuring a first volume of outlet blood flow from the leg in response to said subsequently sequentially restricting step; and comparing the first volume of outlet blood flow to a total volume of outlet blood flow to determine competence of the deep veins below the second location on the leg.

10. A non-invasive method for measuring venous blood output from a leg of a patient which simulates the repair of a valve in the leg, the method comprising:

causing a patient to perform a first tip-toe exercise, wherein venous blood moves from an ankle to an upper thigh in a leg of the patient;

determining a first volume of outlet blood flow through a vein proximate the upper thigh in response to the first tip-toe exercise;

causing a patient to perform a second tip-toe exercise, wherein venous blood moves from the ankle to the upper thigh;

immediately after the second tip-toe exercise, restricting venous blood flow at a first location between the ankle and the upper thigh, wherein said restricting step is performed substantially at the same time and after the venous blood has moved from the first location towards the thigh;

determining a second volume of outlet blood flow through a vein proximate the upper thigh in response to the second tip-toe exercise; and comparing the first volume of outlet blood flow to the second volume of outlet blood flow to determine effect of a repair of a venous valve proximate the first location.

11. The method of claim 10, wherein said restricting venous blood flow step includes providing processing means for inflating a cuff positioned proximate the first location and inflating the cuff substantially at the same time and after the venous blood has moved from the first location towards the thigh.

12. The method of claim 10, wherein said determining a first volume of outlet blood flow step includes measuring a diameter of a femoral vein proximate the upper thigh and measuring a flow rate of blood through the femoral vein proximate the upper thigh.

13. A blood flow sensor comprising:

a first pair of crystals one of which is a transmitter and one of which is a receiver;

a second pair of crystals, one of which is a transmitter and one of which is a receiver, directed at 180 degrees to said first pair of crystals;

a rotatable disk, wherein said first pair of crystals and said second pair of crystals are disposed on said rotatable disk;

means for rotating said rotatable disk to place said pairs of crystals into a desired orientation with respect to blood flow; and means for non-invasively mounting said rotatable disk and said means for rotating externally to a patient proximate a blood vessel in which blood flow is to be measured.

14. The sensor of claim 13, wherein the first pair of crystals is configured at an angle from thirty to forty-five degrees of incidence to the blood vessel.

15. The sensor of claim 13, further comprising a controller connected to said first pair of crystals and said second pair of crystals, said controller includes a means for providing a pulsed signal to said first pair of crystals and said second pair of crystals.

16. The sensor of claim 15, wherein said controller further comprises means for measuring the distance between a first wall and a second wall of the blood vessel.

17. The sensor of claim 16, wherein said controller further comprises means for centering the pulsed sound signal between the first wall and the second wall of the blood vessel.

18. A flow sensor comprising:

a housing having a rotor;

a mounting surface secured to the rotor within said housing;

a first crystal disposed on said mounting surface at a thirty to forty-five degree angle;

a second crystal disposed on said mounting surface at a thirty to forty-five degree angle and positioned adjacent to said first crystal;

a third crystal disposed on said mounting surface at a thirty to forty-five degree angle and directed 180 degrees opposite in direction to said first crystal;

a fourth crystal disposed on said mounting surface at a thirty to forty-five degree angle and directed 180 degrees opposite in direction to said second crystal and positioned adjacent to said third crystal; and a processor configured to emit a first signal from said first crystal and to emit a second signal for said third crystal, wherein the processor detects the first signal in the second crystal and detects the second signal in the fourth crystal.

19. The sensor of claim 18, wherein said processor is further configured to actuate the rotor to rotate the mounting surface to align the first crystal and third crystal along an axis of a vessel.

20. A test system comprising:

inflatable cuffs;

inflation tubes connected to the inflatable cuffs;

a manifold having valves in fluid communication with said inflation tubes;

a pressurized source in fluid communication with said manifold;

a transducer producing a signal representing a parameter of a blood vessel; and a processor controlling the valves of said manifold to inflate and deflate the cuffs and receiving the signal from the transducer so as to determine the location of an incompetent valve in the vessel.

21. The test system of claim 20, wherein said transducer measures the Doppler frequency shift caused by fluid flow in the vessel.

22. The test system of claim 20, wherein said processor includes means for sequentially opening and closing the valves of said manifold.

23. The test system of claim 22, wherein said cuffs are configured to conform to a leg of a patient.

24. The test system of claim 23, means for displaying information from said processor.

25. The test system of claim 20, further comprising a test station for reclinably positioning a patient, upon which said processor and said manifold are mounted.

26. A method for measuring wall-to-wall dimensions of a blood vessel, the method comprising:

providing a first pair of crystals configured to send and receive sound signals;

providing a second pair of crystals configured to send and receive sound signals, wherein the second pair of crystals is rotated 180 degrees from the first pair of crystals;

generating a pulsed sound signal of a measurable frequency through the first and second crystals pairs, wherein the sound signal is directed to a first wall and a second wall of a blood vessel;

detecting a reflected sound signal in each of the crystals pairs, wherein the Doppler shift in the frequency of the reflected sound signal from the pulsed sound signal is measured; and determining the distance between the first wall and the second wall of the blood vessel as a function of the Doppler shift measured in each of the crystal pairs.

27. A method for measuring fluid flow rate in a vessel, the method comprising:

providing a first pair of crystals configured to send and receive sound signals;

providing a second pair of crystals configured to send and receive sound signals, wherein the second pair of crystals is fixed at a rotation 180 degrees from the first pair of crystals;

generating a pulsed sound signal of a measurable frequency through the first and second crystals pairs, wherein the sound signal is directed to fluid flowing within a vessel;

detecting a reflected sound signal in each of the crystals pairs, wherein the Doppler shift in the frequency of the reflected sound signal from the pulsed sound signal is measured;

rotating said first crystal pair and the second crystal pair until the frequency shift measured in the first crystal pair is equal to, but opposite in direction to, the frequency shift measured by the second crystal pair;

and determining the velocity of fluid flow in the vessel as a function of the frequency shift measured by each crystal pair.

28. The method of claim 27, further comprising the steps of determining the distance between a first wall and a second wall of the blood vessel based on the Doppler shift measured in each of the crystal pairs and determining the volumetric flow as a function of the velocity of fluid flow in the vessel and the distance between the walls of the vessel.

29. A blood flow sensor comprising:

a first pair of crystals;

a second pair of crystals directed at 180 degrees to said first pair of crystals;

a rotatable disk, wherein said first pair of crystals and second pair of crystals are disposed upon said rotatable disk;

means for rotating said rotatable disk;

means for mounting said rotatable disk and said means for rotating externally to a patient proximate a blood vessel in which blood flow is to be measured;

a controller coupled to said first pair of crystals and said second pair of crystals including a generator means for providing a pulsed sound signal and a measuring means for measuring a distance between a first wall and a second wall of the blood vessel.

30. The sensor of claim 29, wherein said controller further includes a centering means for centering the pulsed sound signal between the first wall of the blood vessel and the second wall of the blood vessel.

31. A blood flow sensor system for measuring the rate of flow of blood through a selected blood vessel in a patient's limb, comprising:

a mount adapted to be located at a fixed position on the external surface of the patient's limb proximate said selected blood vessel;

a disk rotorably connected to said mount;

a first Doppler transducer affixed to said disk;

a second Doppler transducer affixed to said disk at a position spaced apart from said first Doppler transducer;

a rotation device coupled to said disk for rotating the disk and the transducers on said disk in relation to said blood vessel;

a processor connected to the rotation device for providing control signals to the rotation device to rotate the device so that the first Doppler transducer is located such that blood flow through the blood vessel is directed toward the first Doppler transducer and blood flow through the blood vessel is directed away from the second Doppler transducer.

32. The blood flow sensor system of claim 31 wherein the processor is connected to the Doppler transducers for comparing the Doppler shift sensed by the transducers to each other and providing control signals to the rotation device to rotate the transducers until the Doppler shifts are equal in magnitude and opposite in direction.

33. The blood flow sensor system of claim 31 wherein the processor generates an alarm signal indicating to the user that the Doppler shifts sensed by the first and second transducers are not equal in magnitude and opposite in direction.

34. A system for determining venous competence of a patient comprising:

a plurality of longitudinally spaced-apart inflatable cuffs adapted to be mounted to the patient extending from a first location to a second location, the cuffs adapted to constrict venous blood vessels when inflated to move blood through the vessels;

a sensor located externally on the patient proximate a last location and adapted to generate signals representing sensed blood flow through a vessel; and a controller coupled to the sensor and to the plurality of cuffs, the controller adapted to sequentially inflate the cuffs from the first location to the second location such that venous blood is moved from the first location to the second location, to release the cuffs between the first location and the second location to permit venous blood to flow from the second location to the first location, and to sequentially inflate the cuffs from the second location to the last location such that venous blood is moved from the second to the last locations, the controller further being adapted to receive the signals from the sensor and based upon the signals, to calculate the venous blood output while the cuffs are sequentially inflated from the second to the last locations, and to compare the volume of blood output from the second to the last locations to a total volume of blood output to determine venous competence.

35. The apparatus of claim 34 wherein the controller is configured to determine the size of the vessel a the last location and calculate the venous blood output based upon the determined size.

36. A test system comprising:

inflatable cuffs;

inflation tubes connected to the inflatable cuffs;

a manifold having valves in fluid communication with said inflation tubes;

a pressurized source in fluid communication with said manifold;

a transducer capable of producing a signal based on a Doppler frequency shift caused by fluid flow in a vessel; and a processor controlling the valves of said manifold to inflate and deflate the cuffs, and receiving the signal from the transducer.

37. The test system of claim 36, wherein said processor includes means for sequentially opening and closing the valves of said manifold.

38. The test system of claim 36, wherein said cuffs are configured to conform to a leg of a patient, and said processor includes means for determining the location of an incompetent valve in a vein in the leg.

39. The test system of claim 36, further comprising means for displaying information from the processor.

40. The test system of claim 36, further comprising a test station for reclinably positioning a patient, upon which said manifold is mounted.

* * * * *

UNITED STATES PATENT AND TRADEMARK OFFICE
CERTIFICATE OF CORRECTION

PATENT NO. : 5,730, 136
DATED : Mar. 24, 1998
INVENTOR(S) : Michael D. Laufer, Gary H. Miller It is certified that error appears in the above-identified patent and that said Letters Patent is hereby corrected as shown below:

Column 16, Claim 35, Line 51, after "vessel", change "a", to read --at--.

Signed and Sealed this

Eighth Day of September, 1998

Attest:

BRUCE LEHMAN

Attesting Officer

Commissioner of Patents and Trademarks